US006749810B2

(12) United States Patent
Carr et al.

(10) Patent No.: US 6,749,810 B2
(45) Date of Patent: Jun. 15, 2004

(54) METHOD AND APPARATUS FOR PRESENTING GRAIN FOR NIR SPECTOGRAPHY EXAMINATION

(75) Inventors: Brian W. Carr, Nevada, IA (US); Peter B. Moore, Ames, IA (US); Donald F. Handorf, Ames, IA (US); Timothy A. Schroeder, Ames, IA (US); Nick Merfeld, Nevada, IA (US); Chester S. Creswick, Newton, IA (US); Arlan W. Sandvik, Nevada, IA (US); Gary W. Clem, Nevada, IA (US)

(73) Assignee: Gary W. Clem, Inc., Nevada, IA (US)

( * ) Notice: Subject to any disclaimer, the term of this patent is extended or adjusted under 35 U.S.C. 154(b) by 317 days.

(21) Appl. No.: 09/883,768

(22) Filed: Jun. 19, 2001

(65) Prior Publication Data

US 2001/0055810 A1 Dec. 27, 2001

Related U.S. Application Data

(60) Provisional application No. 60/213,235, filed on Jun. 20, 2000.

(51) Int. Cl.[7] ............................................... G01N 21/29
(52) U.S. Cl. ................................. 422/82.05; 422/82.09; 436/52; 436/173
(58) Field of Search ............................ 436/20, 52, 171, 436/173; 422/82.05, 82.09; 73/866

(56) References Cited

U.S. PATENT DOCUMENTS

| 4,915,827 | A | * | 4/1990 | Rosenthal ..................... 209/577 |
| 5,751,421 | A |   | 5/1998 | Wright et al. |
| 5,991,025 | A | * | 11/1999 | Wright et al. ................. 356/328 |
| 6,418,805 | B1 | * | 7/2002 | Carney et al. .................. 73/866 |
| 6,421,990 | B1 | * | 7/2002 | Ohlemeyer et al. ......... 56/10.2 R |
| 6,483,583 | B1 | * | 11/2002 | Wright et al. ................. 356/326 |
| 6,559,655 | B1 | * | 5/2003 | Rosenthal et al. ............ 324/634 |

* cited by examiner

*Primary Examiner*—Jill Warden
*Assistant Examiner*—LaToya I. Cross

(57) ABSTRACT

The method for presenting grain for NIR spectography examination includes causing the grain to move downward across a sloping presentation surface; associating the optics of an NIR spectography apparatus with the presentation surface to permit light from the optics to be projected into the curtain of grain at a substantial right angle with respect to the direction of flow of the curtain of grain over the presentation surface. An apparatus for presenting grain for NIR spectography examination includes the structure for practicing the aforementioned method.

4 Claims, 2 Drawing Sheets

METHOD AND APPARATUS FOR PRESENTING GRAIN FOR NIR SPECTOGRAPHY EXAMINATION

CROSS-REFERENCE TO RELATED APPLICATIONS

This application is based upon Applicant's Provisional Patent Application Ser. No. 60/213,235 filed on Jun. 20, 2000.

BACKGROUND OF THE INVENTION

The use of infrared spectroscopy (NIR) for analyzing grain is a conventional technique for detecting microconstituents of the grain including protein, oil, moisture, starch, acids, etc. This technology has previously been used in conjunction with harvesting combines.

However, existing disclosures of this combination, particularly with combines used in conjunction with research plots have certain shortcomings. For example, it is useful to conduct the NIR process through a moveable layer or curtain of grain which is adjustable in its thickness and thick enough not to allow light from the NIR optics to easily and fully penetrate the curtain of grain. It is further desirable to not only be able to adjust the thickness of the layer of grain, but to increase this thickness at such times as debris impairs the free flow of the curtain of grain over the NIR optic system. It is a further advantage to completely isolate the curtain of grain and the NIR optics from ambient light.

It is therefore a principal object of this invention to have a computer-controlled system for conducting NIR spectography which is adaptable for harvesting combine usage which will disburse a layer of grain over an inclined presentation surface for examination by the optics of the NIR system.

A further object of this invention is to isolate the presentation surface from ambient light so as not to interfere with the NIR optic equipment.

It is still a further object of this invention to provide an NIR spectography system which can evaluate moving grain quickly and which can do so in selective quantities which are separate and which are efficiently moved through the apparatus in the interest of conservation of time as would be necessary in the case of using the equipment on a moving harvesting combine.

These and other objects will be apparent to those skilled in the art.

SUMMARY OF THE INVENTION

The method for presenting grain for NIR spectography examination includes placing a quantity of grain to be examined in an overhead compartment with a lower grain discharge port; causing the grain to move downward through the discharge port in a curtain of grain of measured thickness; depositing the curtain of grain for downward movement across a sloping presentation surface; associating the optics of an NIR spectography apparatus with the presentation surface to permit light from the optics to be projected into the curtain of grain at a substantial right angle with respect to the direction of flow of the curtain of grain over the presentation surface; and gathering data from energy reflected towards the NIR spectography apparatus for analysis of microconstituents within the grain comprising the curtain of grain.

An apparatus for presenting grain for NIR spectography examination includes an overhead grain compartment with a lower grain discharge port. A valve in the port permits selective opening and closing. A sloping wall is presented in a grain channel located below the port, and grain from the port is deposited on the sloping presentation surface. A moveable baffle element is located in the grain channel to control the thickness of the grain curtain. The optics of an NIR spectography apparatus is associated with the presentation surface to permit light from the optics to be projected into the curtain of grain passing over the inclined presentation surface. The light is emitted at a substantial right angle with respect to the directional flow of the curtain of grain over the presentation surface. The controller is associated with the foregoing components to coordinate their various functions.

DESCRIPTION OF THE PREFERRED EMBODIMENT

Figure 1:
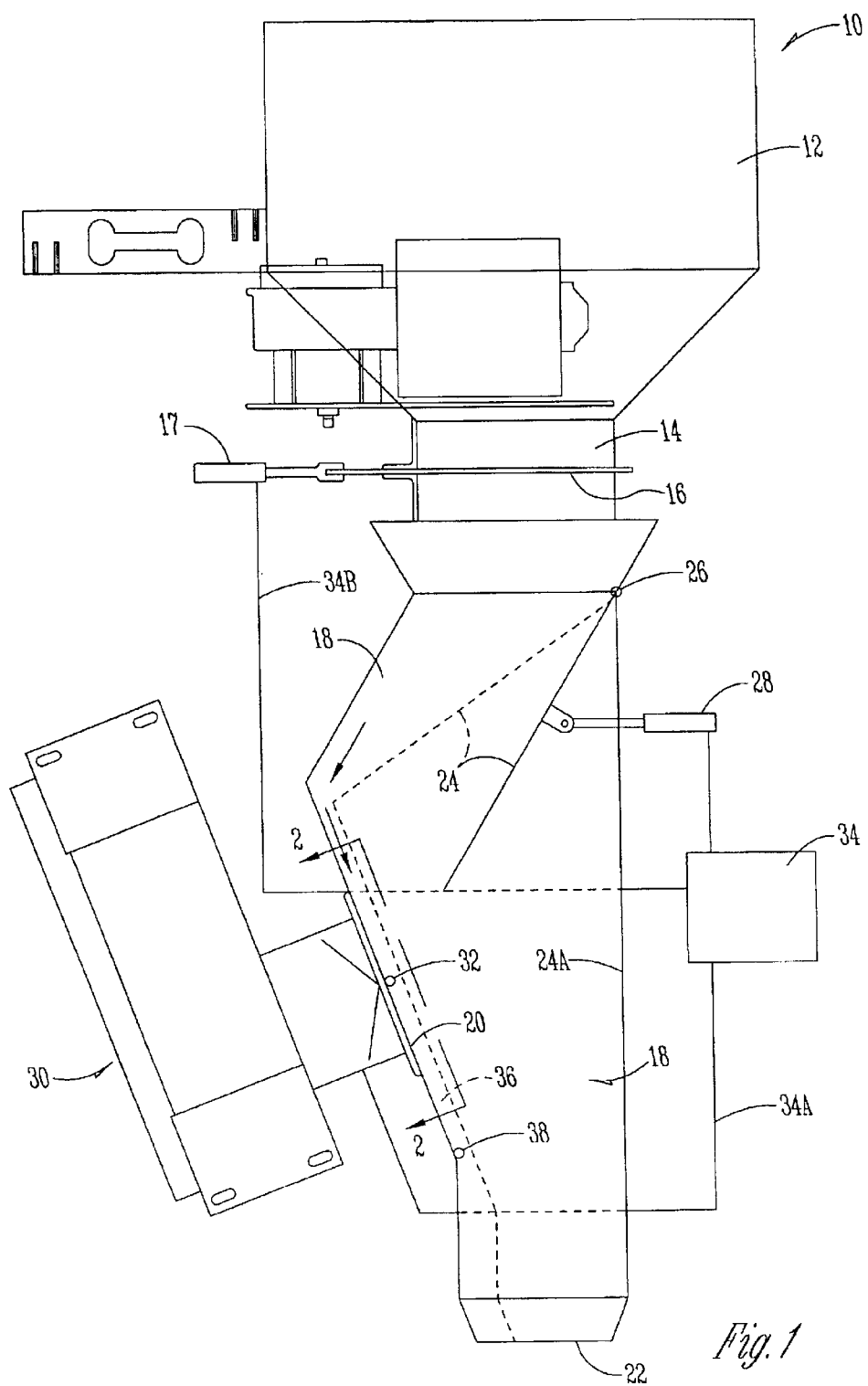
FIG. 1 is a schematic view of the apparatus and method of this invention.
Figure 2:
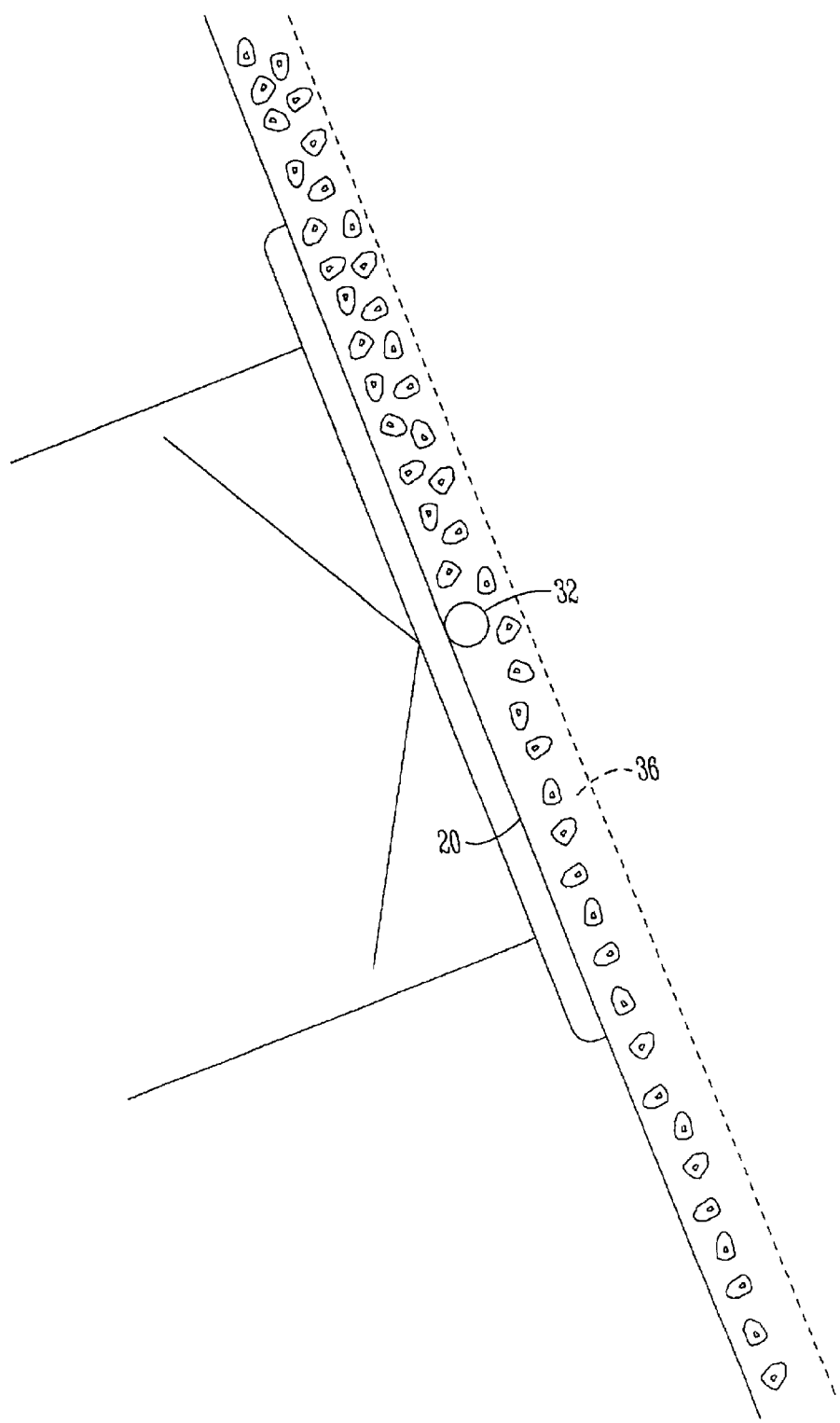
FIG. 2 is an enlarged scale view of a portion of FIG. 1 taken on line 2—2 of FIG. 1.

The apparatus 10 consists of a grain compartment 12 having an outlet port 14. When mounted in a combine, the apparatus 10 receives harvested grain directly from the harvesting mechanism of the combine. This can either be a continuous supply of grain that is provided to the compartment, or specific independent separate samples can be sequentially delivered to the compartment 12. Outlet port 14 is located in the lower end of grain compartment 12.

A conventional slide valve 16 is mounted within port 14 and is controlled by any conventional slide valve actuator 17.

A grain channel 18 extends downwardly from below the port 14 and includes a sloping surface 20 which can be comprised of a layer of transparent material such as glass. The channel 18 has a lower discharge end 22.

A baffle 24 is hinged to channel 18 by means of hinge 26. A conventional baffle actuator 28 pivots baffle 24 about hinge 26 to move the baffle towards or away from the sloping surface 20.

The conventional NIR spectography apparatus 30, such as available from Carl Ziss Jena GmbH of Jena, Germany. The NIR apparatus 30 has an optic system 32 which can either be located within channel 18 or can be embedded within the sloping surface 20 with light access into the channel 18.

A control 34 is connected by leads 34a, 34b, and 34c to the NIR apparatus 30, the valve actuator 17, and the baffle actuator 28, respectively, so as to control these various components. A curtain of grain 36 shown by the dotted lines in the drawings can be created by movement of the baffle 24 towards or away from the sloping surface 20 to provide a flow of grain of uniform thickness past the optic system 32 of the NIR apparatus 30.

A sensor 38 can also be connected to controller 34 (connection not shown) to detect an interruption in the curtain of grain 36 which may be caused by debris or the like at the lower end of the baffle member 24.

In operation, separate samples of grain can be continuously but independently deposited into compartment 12. To start the process, the controller actuates the member 17 to open the port 14 whereupon a flow of grain moves downwardly into channel 18. Baffle 24 is moved to a predetermined position shown by the dotted lines in the drawings to create a curtain of grain 36 which is deposited on the sloping surface 20 to create the curtain of grain 36 of predetermined thickness. The movement of the grain moves over and past the optic system 32 of the NIR apparatus 30 whereupon the NIR apparatus performs its conventional function. The output from the NIR apparatus is not shown but it reveals conventionally the various microconstituents of the grain passing therethrough. Any light that penetrates the layer of grain will be reflected against the wall 24a opposite to the sloping surface 20. Because the sloping surface 20 and the wall 24a are not parallel, any light from the optic system 32 will not be reflected directly back towards the optic system 32.

If any debris gathers at the lower end of the baffle 24 as shown by the dotted lines in the drawings, the interrupted curtain of grain 36 will be detected by the sensor 38 which will cause the controller to quickly open and then close the baffle 24 so as to permit the debris to flow through and whereupon the flow of the normal curtain of grain 36 will be resumed. The controller 34 will close the valve 16 by actuating controller 17 when a first sample of grain has passed through. As soon as the curtain of grain from the first sample is purged from the channel 18, the next sample of grain will be deposited in the compartment 12, and the process will quickly and efficiently resume.

While the apparatus of this invention can be placed on a harvesting combine, it should also be understood that this apparatus is useful in other environments wherever seed is being processed, stored, or otherwise handled such as at grain elevators or the like.

It is therefore seen that this invention will achieve at least all of its stated objectives.

We claim:

1. An apparatus for presenting grain for NIR spectography examination, comprising,
    an overhead grain compartment having a lower grain discharge port,
    a closeable valve on the discharge port,
    a downwardly extending grain channel located below the discharge port and adapted to receive grain from the overhead compartment when the valve is open,
    the channel including a sloping presentation surface,
    the sloping surface is comprised of a transparent material,
    an adjustable baffle in the channel adapted to direct a curtain of grain of uniform thickness from the overhead compartment into engagement with the sloping presentation surface,
    the channel having a discharge opening at a lower end,
    and an NIR spectography apparatus associated with the presentation surface and including an optic system to direct light at a substantial right angle with respect to the direction of flow of the curtain of grain over the presentation surface for analysis of the microconstituents within the grain comprising the curtain of grain.

2. An apparatus for presenting grain for NIR spectography examination, comprising,
    an overhead grain compartment having a lower grain discharge port,
    a closeable valve on the discharge port,
    a downwardly extending grain channel located below the discharge port and adapted to receive grain from the overhead compartment when the valve is open,
    the channel including a sloping presentation surface,
    an adjustable baffle in the channel adapted to direct a curtain of grain of uniform thickness from the overhead compartment into engagement with the sloping presentation surface,
    the channel having a discharge opening at a lower end,
    an NIR spectography apparatus associated with the presentation surface and including an optic system to direct light at a substantial right angle with respect to the direction of flow of the curtain of grain over the presentation surface for analysis of the microconstituents within the grain comprising the curtain of grain, and
    the optics of the NIR spectography system is located within the sloping surface and is in communication with the channel so as to be in direct contact with a curtain of grain moving over the sloping surface.

3. An apparatus for presenting grain for NIR spectography examination, comprising,
    an overhead grain compartment having a lower grain discharge port,
    a closeable valve on the discharge port,
    a downwardly extending grain channel located below the discharge port and adapted to receive grain from the overhead compartment when the valve is open,
    the channel including a fixed sloping presentation surface,
    the sloping surface is comprised of a transparent material,
    an adjustable baffle in the channel adapted to direct a curtain of grain of uniform thickness from the overhead compartment into engagement with the sloping presentation surface,
    the channel having a discharge opening at a lower end,
    and an NIR spectography apparatus associated with the presentation surface and including an optic system to direct light at a substantial right angle with respect to the direction of flow of the curtain of grain over the presentation surface for analysis of the microconstituents within the grain comprising the curtain of grain.

4. The apparatus of claim 3 wherein the optics of the NIR spectography system is located within the sloping surface and is in communication with the channel so as to be in direct contact with a curtain of grain moving over the sloping surface.

* * * * *